United States Patent [19]

Pucci et al.

[11] Patent Number: 4,582,811

[45] Date of Patent: Apr. 15, 1986

[54] METHOD AND DIAGNOSTIC AID FOR DETECTING OCCULT FAECAL BLOOD

[75] Inventors: Alessandra Pucci; Antony M. Smithyman; Martin B. Slade; Peter W. French; Gene Wijffels, all of Sydney, Australia

[73] Assignee: Australian Monoclonal Development Pty. Ltd., New South Wales, Australia

[21] Appl. No.: 575,806

[22] Filed: Feb. 1, 1984

[30] Foreign Application Priority Data

Feb. 2, 1983 [AU] Australia .............................. 10958/83

[51] Int. Cl.4 ...................... G01N 33/54; G01N 1/48; G01N 21/06; G01N 31/22
[52] U.S. Cl. .......................................... 436/548; 435/7; 435/805; 436/66; 436/531; 436/810; 422/56
[58] Field of Search ................. 436/548, 810, 66, 531; 435/7, 805; 422/56

[56] References Cited

U.S. PATENT DOCUMENTS

| 3,630,957 | 12/1971 | Rey et al. ............................... 436/66 |
| 3,641,235 | 2/1972 | Weiss ................................... 436/810 |
| 4,135,884 | 1/1979 | Shen ..................................... 436/810 |
| 4,196,265 | 4/1980 | Koprowski et al. ................. 436/548 |
| 4,427,769 | 1/1984 | Adlercreutz et al. .............. 436/810 |

Primary Examiner—Sidney Marantz
Assistant Examiner—L. Krawczewicz
Attorney, Agent, or Firm—Kane, Dalsimer, Kane, Sullivan & Kurucz

[57] ABSTRACT

A diagnostic aid for use in detecting occult blood in faeces is described. The aid consists of a carrier which is coated with specific monoclonal anti-human antibody and, which upon contact with a faecal liquid suspension, specifically absorbs human hemoglobin. A chemical or an enzymatic assay may then be used to detect the hemoglobin.

9 Claims, 2 Drawing Figures

METHOD AND DIAGNOSTIC AID FOR DETECTING OCCULT FAECAL BLOOD

This invention concerns a diagnostic aid for use in detecting occult blood in faeces.

The presence of blood in faeces may be indicative of intestinal lesions, frequently of carcinoma. Early detection of intestinal bleeding is therefore useful in the screening for colorectal cancer, one of the major killer diseases in industrialized countries.

The screening became widespread when Greegor showed that early, asymptomatic colorectal carcinoma could be diagnosed by systematic testing of faeces for occult blood, and by subsequent investigation of those found to be positive.

Commercial diagnostic kits were therefore prepared and used by pathologists and general practitioners. The operation of currently available kits is based on a chemical reaction that is catalysed by hemoglobin, the major protein contained in blood.

Although simple to use, these kits have several shortcomings. Sensitivity and specificity are the main problems and lack of either leads to false negatives and false positives. In some studies it was shown that false results may be as high as 75%. Lack of sensitivity, and the resulting false negative results depends on the inability of a certain test to detect low levels of hemoglobin. Agents such as vitamin C also interfere and cause false negative reactions. False negative results have serious consequences since early diagnosis of cancer is critical for survival.

Lack of specificity and false positives are a much greater technical problem. In the tests mentioned above this is caused by similar chemical reactions which are not due to human hemoglobin activity. For one, vegetable proteins and hemoglobin or myoglobin derived from ingested animal meat may interfere with the reaction. In other cases, activity of the bacterial flora causes a similar reaction. Dietary instructions are inconvenient and not easy to follow strictly. In addition, it is not possible to control the reaction of bacteria and its interference.

These and other minor problems associated with current commercial kits have encouraged different approaches to research. As a consequence, a number of immunochemical assays have been devised to improve the sensitivity and in particular the specificity of testing.

A radial immunodiffusion assay has been developed using antibodies to hemoglobin. These are prepared in rabbits and are extensively absorbed to purify the monospecific fraction that reacts only with human hemoglobin. The preparation is elaborate and each batch has to be evaluated for cross-reactivity and sensitivity before use. In addition, the test procedure itself is not simple, it involves a number of delicate steps and takes 24 hours to read. It is therefore unlikely that this test may be applied for large screening programs.

Another immunochemical assay has been devised in the form of an immuno-fluorescent test. It makes use of fluorescein-labelled rabbit anti-human hemoglobin serum which is mixed with the faecal suspension and later read in a fluorometer. While the preparation of the antisera, because of the need to extensively test each batch produced, is time consuming and will in a large production bear on the price. The test itself is automated and simple to administer. Sensitivity however may be a problem since the quantitative evaluation, based on an inhibition assay, is not clearcut under 5 mg of hemoglobin/g faeces, which is well above the normal upper limit of 1.8 mg/g.

A third immunochemical assay has been devised and is based on an Enzyme Linked Immunosorbant assay (ELISA) which is very sensitive. Its specificity depends on the antiserum used, and is satisfactory when the antisera are extensively treated to become monospecific. The test itself is quite elaborate and would not be of general use to medical practitioners.

Finally, a manual immuno-nephelometric method for quantitative assay of free hemoglobin in plasma and urine has been described in the literature.

In general, the immunochemical assays, while representing an improvement on the chemical tests currently available, in turn need to be improved by the use of more reliable antisera and by the simplification of procedures. In addition, these assays have not yet been developed in testing kits.

This invention seeks to provide an aid for detecting occult faecal blood which depends for its efficiency upon an assay technique which is different from those described above.

This invention provides a diagnostic aid for use in detecting occult faecal blood consisting of a carrier which binds protein, the surface of which carrier is at least partly coated with monoclonal antibody which is specific for human hemoglobin.

The carrier may be synthetic plastic for example polyvinyl chloride, polystyrene or nylon; glass and nitro cellulose films are also suitable. A dipstick represents a simple hygienic carrier for absorbing hemoglobin from the faeces. The dipstick may be made of polystyrene which amongst others is known to attach proteins. The stick is therefore coated with our specific antihuman hemoglobin antibody which, upon contact with a faecal liquid suspension, will specifically absorb human hemoglobin, if any present, on the surface of the dipstick. The absorption step in this assay is important since all other interfering compounds are washed away. Both the sensitivity and the specificity problems are solved here in one step, allowing the rest of the test to be as simple as required by the tester. This is due to the fine qualities of the monclonal antibody which covers the stick. Once the human hemoglobin present in faeces is absorbed to the stick, a simple chemical reaction or a more complex enzymatic reaction may be applied.

The preparation of the monclonal antibody following the Kohler-Milstein technique, involves (a) immunization of Balb/C mice with purified human hemoglobin (b) hybridization of immune spleen cell with the NSI-myeloma cell line, (c) culture of hybrids, (d) screening of culture supernatants by a computerized ELISA system (e) continuous culture of positive, specific hybrid cell clones, and (f) preparation of high titre ascitic fluid. The main achievement of this technology is that the final specific antibody can be prepared in large quantities in a short time. The need for a large scale production is met by the combination of extremely concentrated fluids and the uniformity of the clone-derived products. Virtually unlimited, qualitatively identified batches can be produced. The development of the specific hybrid clones was complex, lengthy and certainly no less elaborate than the preparation of conventional affinity-purified antisera. The significant difference however, lies in the subsequent industrial production: in the case of conventional antisera the whole process had to be repeated each time, while for the monoclonal antisera, once a specific antibody secreting cell line is developed, production of the antibody is continuous. The advantage of using this monoclonal antibody rather than conventional antisera is therefore one of time and cost saving and extreme specificity.

The development of the monoclonal antibody has entailed the production of large numbers of monoclonal antibodies against hemoglobin and to selection of those which do not react with hemoglobins from any commonly eaten meat (e.g., beef, sheep, horse, rabbit, chicken, pig and kangaroo). Furthermore, as hemoglobin is known to exhibit conformational changes on reacting with oxygen, nitrates, sulphides and drugs which may be present in faeces, it has been necessary to select those antibodies that are able to react with hemoglobin after it has been incubated with faeces. These problems are not apparent with conventional polyclonal serum which may contain some antibodies capable of reacting with each conformational form of hemoglobin. We have produced suitable human specific monoclonal antibodies to both the $\alpha$ and $\beta$ subunits of human hemoglobin enabling the test to take the form of a "sandwich" with antibody to the hemoglobin subunit on the carrier to absorb human hemoglobin which can then be detected with a second monoclonal antibody to another antigenic determinant on the hemoglobin. Our preferred antibody for coating the carriers, called HHb45, specifically reacts with the subunit of human hemoglobin. Antibody HHb45 is a mouse immunoglobulin of class IgG1 and gives several isoelectric focusing bands clustered around pH 5.9 ($\pm 0.2$).

BRIEF DESCRIPTION OF THE DRAWINGS

Two embodiments of the invention are now described, one with reference to the accompanying drawings in which.

Figure 2:
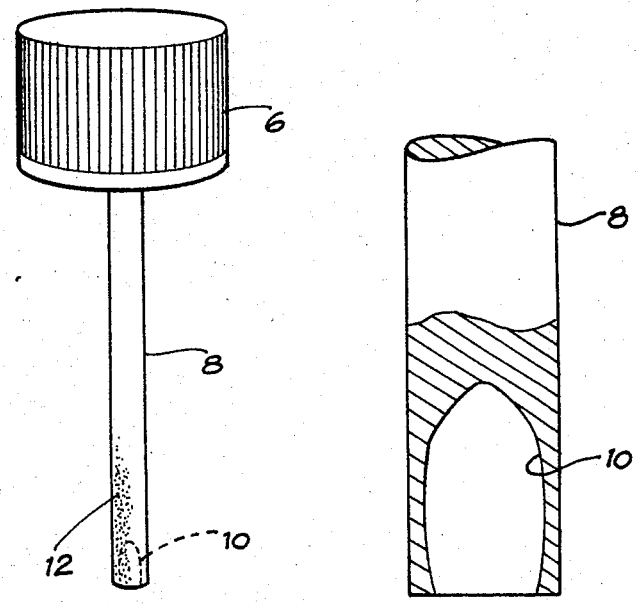
FIG. 2 shows a fragmentary view of the sample-taking end of the dipstick.
Figure 1:
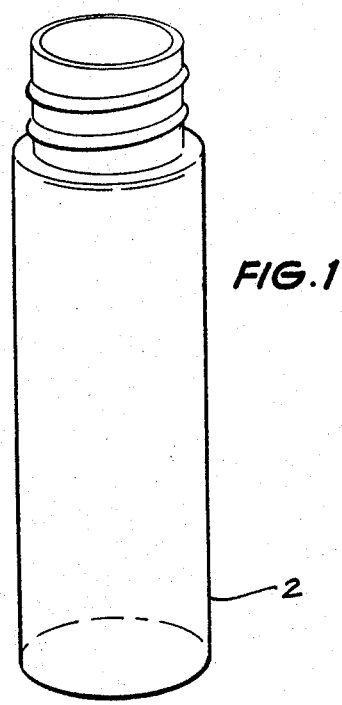
FIG. 1 shows a perspective view of the dipstick and test vessel.

A test bottle 2 made of glass has a threaded top 4 which receives a threaded cap 6 from which extends a solid rod of polystyrene 8 the end of which has a cavity 10 of conical section. The external surface of the rod and cavity is coated with the specific antibody 12. Faeces are stabbed with the dipstick in order to fill the cavity with a plug sample which is washed out of the cavity by shaking with water inside the test bottle. The antibody attracts any human hemoglobin in the sample while allowing other compounds to be washed away.

The dipstick is then transferred into a second test tube containing a washing solution. In a further step, the washed dipstick is transferred to another test tube where the hemoglobin attached to the stick catalyzes a chemical reaction which, if positive will be detected by a change of colour.

For increased sensitivity the chemical reaction can be replaced by an immunochemical reaction where the absorbed hemoglobin is detected by a second antibody to human hemoglobin labelled with an enzyme, a radiochemical, fluorescein, biotin or luminol. The second antibody may be either a monoclonal antibody or a polyclonal serum to hemoglobin, since the specificity of the test is ensured by the specificity of the antibody on the carrier.

In another embodiment, a strip or disk of nitrocellulose membrane, coated with anti-human hemoglobin monoclonal antibody, is placed in a cardboard envelope with a filter paper window for application of the faeces sample. The filter paper retains the faecal solids, but allows the liquids to absorb onto the membrane by capillary action. Following the absorption process, the envelope containing the sample may be stored dry or sent to a central laboratory for processing. In the laboratory the nitrocellulose membrane is transferred to another vessel, washed, and the hemoglobin detected by means of a chemical reaction or a more complex second antibody enzymatic reaction.

We have found the advantage of the above example to be as follows. A dipstick coated with an anti-human hemoglobin monclonal antibody allows a sensitive and specific absorption of this human blood protein on the stick which can be freely used in a colorimetric reaction without further concern for the problems of sensitivity and specificity currently associated with chemical kits. In addition, it allows simple testing with consistent material that is easily produced.

The claims defining the invention are as follows.

We claim:

1. A diagnostic aid for use in detecting occult faecal blood consisting of a carrier (8) which binds protein, the surface of which carrier is at least partly coated with monoclonal antibody (12) which is specific for human hemoglobin.

2. A diagnostic aid as claimed in claim 1 wherein at least that part of the carrier (8) which is intended for immersion during the diagnostic test is made of plastic.

3. A diagnostic aid as claimed in claim 1 wherein at least that part of the carrier (8) which is intended for immersion during the diagnostic test is made of a fibrous material, which binds protein.

4. A diagnostic aid as claimed in claim 1 wherein at least that part of the carrier which is intended for immersion during the diagnostic test is made of a film which binds protein.

5. A diagnostic aid as claimed in claim 2 wherein the carrier (8) is a dipstick the immersible end of which is coated with the antibody.

6. A diagnostic aid as claimed in claims 1 and 2 wherein the carrier is a flat surface, which is attached to a handle and is coated at least in part with the antibody.

7. A diagnostic aid comprising a solid implement for insertion into a test vessel containing liquid to be assayed for the presence of a suspected component which implement comprises a handle part (6) and an immersible part (8) wherein at least the latter part is made of a material which binds protein the immersible part being coated with monoclonal antibody (8) which is specific for human hemoglobin.

8. A diagnostic aid as claimed in claim 1 wherein the antibody carrier is manufactured in the shape of a tube, hollow well or vessel, into which the faecal sample or homogenate is placed.

9. A method of detecting occult faecal blood comprising absorbing hemoglobin from a faecal liquid suspension, by means of anti-human hemoglobin monoclonal antibody located on a carrier, washing residual suspension from the carrier and performing a further test which is specific for hemoglobin upon the hemoglobin on the carrier.

* * * * *